(12) United States Patent
Prange

(10) Patent No.: US 10,245,120 B2
(45) Date of Patent: Apr. 2, 2019

(54) METHOD OF MANUFACTURE OF A DENTAL PROPHY ANGLE

(71) Applicant: Young Innovations, Inc., Earth City, MO (US)

(72) Inventor: Brian Prange, St. Louis, MO (US)

(73) Assignee: Young Innovations, Inc., Earth City, MO (US)

( * ) Notice: Subject to any disclaimer, the term of this patent is extended or adjusted under 35 U.S.C. 154(b) by 270 days.

(21) Appl. No.: 15/433,897

(22) Filed: Feb. 15, 2017

(65) Prior Publication Data

US 2018/0228573 A1 Aug. 16, 2018

(51) Int. Cl.
| | |
|---|---|
| *A61C 1/00* | (2006.01) |
| *A61C 17/00* | (2006.01) |
| *B29C 65/00* | (2006.01) |
| *A61C 1/16* | (2006.01) |
| *A61C 1/12* | (2006.01) |
| B29C 65/48 | (2006.01) |
| B29C 65/08 | (2006.01) |
| B29L 31/00 | (2006.01) |

(52) U.S. Cl.
CPC ............. *A61C 1/16* (2013.01); *A61C 1/12* (2013.01); *A61C 17/005* (2013.01); *B29C 65/08* (2013.01); *B29C 65/48* (2013.01); *B29C 66/1122* (2013.01); *B29C 66/532* (2013.01); *B29C 66/71* (2013.01); *B29C 66/712* (2013.01); *B29C 66/73152* (2013.01); *B29C 66/73921* (2013.01); *B29L 2031/753* (2013.01)

(58) Field of Classification Search
CPC .... A61C 1/00; A61C 1/10; A61C 1/16; A61C 1/12; A61C 17/00; A61C 17/005; B29C 65/00; B29C 65/08; B29C 65/40; B29C 65/48; B29C 66/00; B29C 66/70; B29C 66/71; B29C 66/71; B29C 66/712
See application file for complete search history.

(56) References Cited

U.S. PATENT DOCUMENTS

| | | | | |
|---|---|---|---|---|
| 5,131,846 A | * | 7/1992 | Hall | A61C 1/16 433/116 |
| 8,784,102 B1 | * | 7/2014 | Kumar | A61C 1/141 433/166 |
| 2012/0034575 A1 | * | 2/2012 | Tarr | A61C 17/005 433/82 |

\* cited by examiner

*Primary Examiner* — Jacob T Minskey
*Assistant Examiner* — Matthew Hoover
(74) *Attorney, Agent, or Firm* — Timothy M. McCarthy; Clark Hill PLC

(57) ABSTRACT

A method of manufacturing a dental prophy angle with a wiper assembly is described. The prophy angle comprises a neck section and the neck section has an outer surface. The method comprises the steps of manufacturing a dental prophy angle, manufacturing a wiper assembly by molding a base, the base having an undersurface, the undersurface configured to match the outer surface of the neck section, molding a shield, the shield assembly comprising a carriage and a wiper, attaching the base to the shield assembly, and attaching the undersurface to the outer surface.

14 Claims, 3 Drawing Sheets

METHOD OF MANUFACTURE OF A DENTAL PROPHY ANGLE

FIELD OF THE INVENTION

This invention relates generally to the manufacture of devices used in the dental profession.

BACKGROUND OF THE INVENTION

Two basic problems that are addressed during a patient's routine visit to a dentist are plaque and tartar (also called calculus). (The term "dentist" for purposes of this application includes a doctor of dental surgery, a periodontist, a dental hygienist, a dental assistant, a veterinarian, a veterinary dentist, a veterinary assistant, or any other person who treats teeth for plaque, tartar, or related problems. The term "patient" means a being with teeth, and includes humans and non-humans, including but not limited to dogs, horses, or other animals who need dental treatment.)

Plaque is a sticky biofilm while tartar is a crusty deposit. Removal of plaque and tartar usually involves one or both of two elementary procedures for cleaning the patient's teeth. A dentist will scale the teeth by mechanically removing plaque which has formed as calculus on the surface of the teeth. Scaling can be done using hand tools or power scaling tools. Polishing is the removal of plaque and the smoothing of the surfaces of the teeth to make it difficult for plaque to attach. Polishing is usually done after scaling but can be done first if the dentist chooses. Polishing is conventionally accomplished by use of a prophy angle, a dental device which has a rotating rubber cup at the end of a dental handpiece, a motorized tool. The dentist uses the prophy angle to apply a prophy paste to clean and polish the tooth surfaces mechanically.

A prophy angle as is known in the prior art has three sections attached in this order: a neck section, a grip section, and a drive section. The motor or turbine on a dental handpiece attaches to the drive shaft of the prophy angle, which extends axially from the drive section through the grip section and into the neck section. As the dental handpiece is activated, it turns the drive shaft and a driving gear at its forward end inside the neck section. The driving gear interacts with a driven gear located in the neck section. The driven gear rotates the prophy cup. The motor or turbine need power and accordingly have a cord attached to the near end of the drive section, the cord either conveying electricity to the motor or compressed air to the turbine. In some cases, the tool is cordless and contains a battery to power the motor.

The dentist polishes the patient's teeth by dipping the prophy cup into a container of polishing paste and applying the paste to the patient's teeth. The rotation of the prophy cup polishes the teeth, but also tends to splatter the paste. One prior-art solution was the use of vanes or ribs within the prophy cup, as described in U.S. Pat. No. 4,929,180 to Moreschini, Stay Full-Easy Load "Turbo" Prophylactic Polishing Cup and in United States Published Patent Application No. 2008/0076091 to Moreschini, 'Turbo' prophy cup with step like prophy paste collecting reservoirs on turbine like vanes.

Another prior-art solution was to use a wiper to remove slurry as the prophy cup rotates, as described in, for example, U.S. Pat. No. 8,784,102 to Kumar, Prophy Cup for Dental Handpiece.

To manufacture a wiper as known in, for example, the '102 Patent to Kumar, the body of the prophy angle is manufactured in two parts, with a recessed channel in the neck section of the body. The wiper is manufactured separately and is constrained within the recessed channel to position the wiper properly with respect to the prophy cup. The two body parts are then assembled with the gears to create a functioning prophy angle.

Accordingly, to add a wiper to an existing design of a prophy angle, the entire prophy angle must be redesigned. The use of a recessed channel to hold the wiper requires a re-assessment of the space within the neck section, as existing prophy angle designs do not have the recessed channel. Accordingly, to add a wiper to a prophy angle, there must be a redesign of the molds for the two body parts, a redesign of the molds for the driving gear and the driven gear, and a new mold for the wiper. This method is particularly expensive because new molds for high-volume production are costly. A need exists, then, for a method of manufacture of dental appliances and parts that avoids the costs of the prior art.

SUMMARY OF THE INVENTION

The preferred embodiment of the method of the present invention comprises a method of manufacturing a dental prophy angle with a wiper, the prophy angle comprising a neck section and the neck section having an outer surface, the method comprising the steps of manufacturing a dental prophy angle, manufacturing a wiper assembly by molding a base, the base having an undersurface, the undersurface configured to match the outer surface of the neck section, molding a shield assembly, the shield assembly comprising a carriage and a wiper, attaching the base to the shield assembly, and attaching the undersurface to the outer surface.

A BRIEF DESCRIPTION OF THE DRAWINGS

The organization and manner of the structure and operation of the invention, together with further objects and advantages thereof, may best be understood by reference to the following description, taken in connection with the accompanying non-scale drawings, wherein like reference numerals identify like elements in which.

DETAILED DESCRIPTION OF THE ILLUSTRATED EMBODIMENTS

Figure 1:
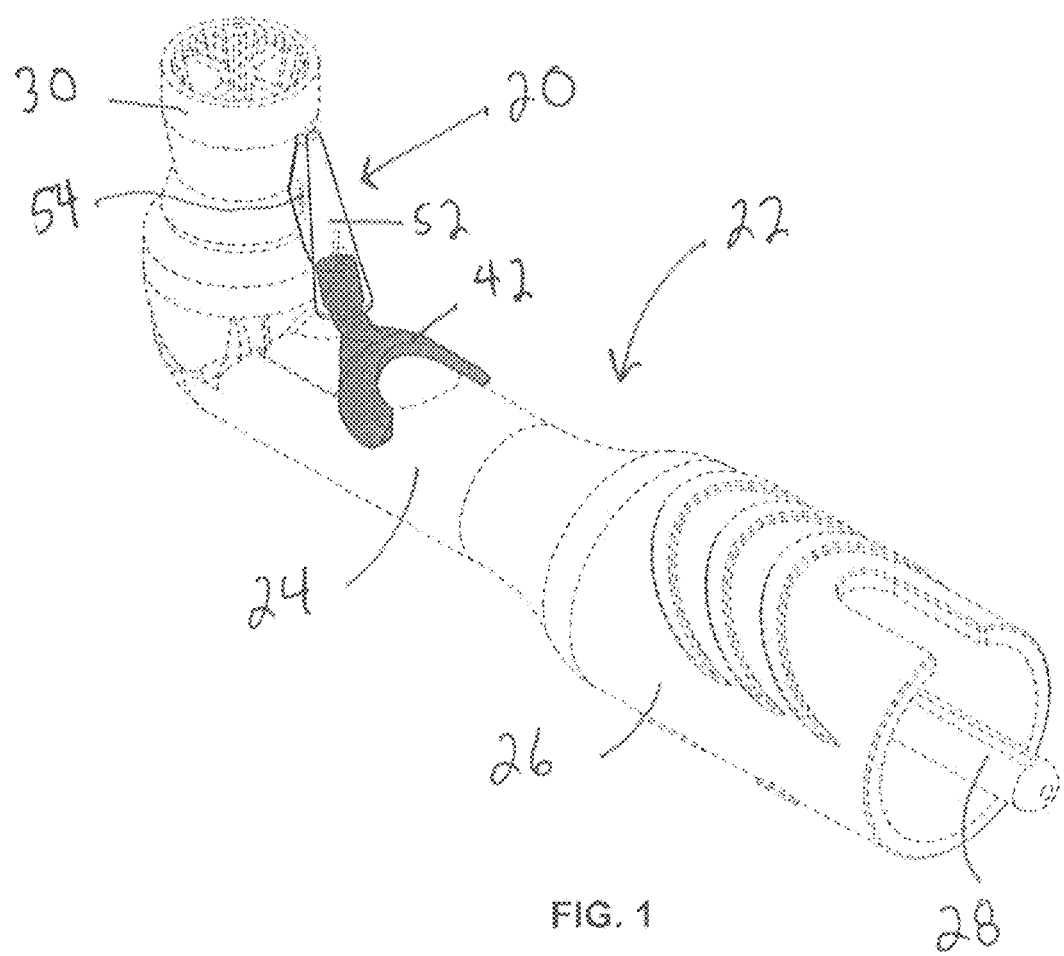
FIG. 1 is a perspective view of the prophy angle manufactured by the method of the present invention.

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

A wiper assembly 20 as manufactured by the method of the present invention is shown in FIG. 1 attached to a prophy angle 22. A neck section 24 and a grip section 26 of prophy angle 22 are illustrated. A drive shaft 28 through grip section 26 and neck section 24 rotates a driving gear (not shown) that interacts with a driven gear (not shown) located in the neck section 24 to rotate a prophy cup 30.

Neck section 24, grip section 26, drive shaft 28, driving gear, and driven gear are all injection molded in a conventional manner. Cup 30 is injection molded or vulcanized. These components are then assembled to form prophy angle 22.

Figure 2:
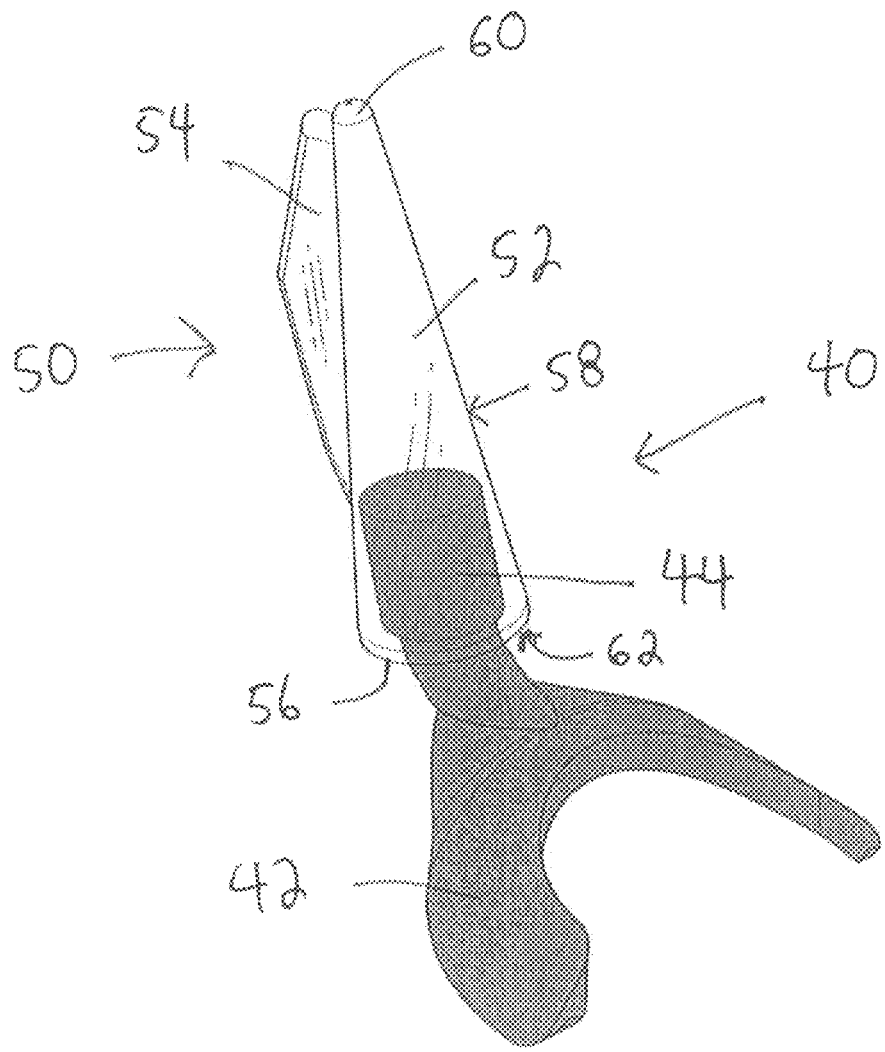
FIG. 2 is a perspective view of the wiper assembly of the prophy angle of FIG. 1.

Wiper assembly 40, as shown in FIG. 2, has a base 42 and a shield assembly 50. Base 42 is a structure configured to conform to the shape of neck section 24. A boss 44 extends radially from base 42. Boss 44 is preferably cylindrical but may have other shapes.

As illustrated, base 42 is a U-shaped structure for aesthetic reasons. Base 42 has an undersurface that conforms to the surface of neck section 24, to facilitate attachment, but can be any shape that accommodates such an undersurface.

Figure 3:
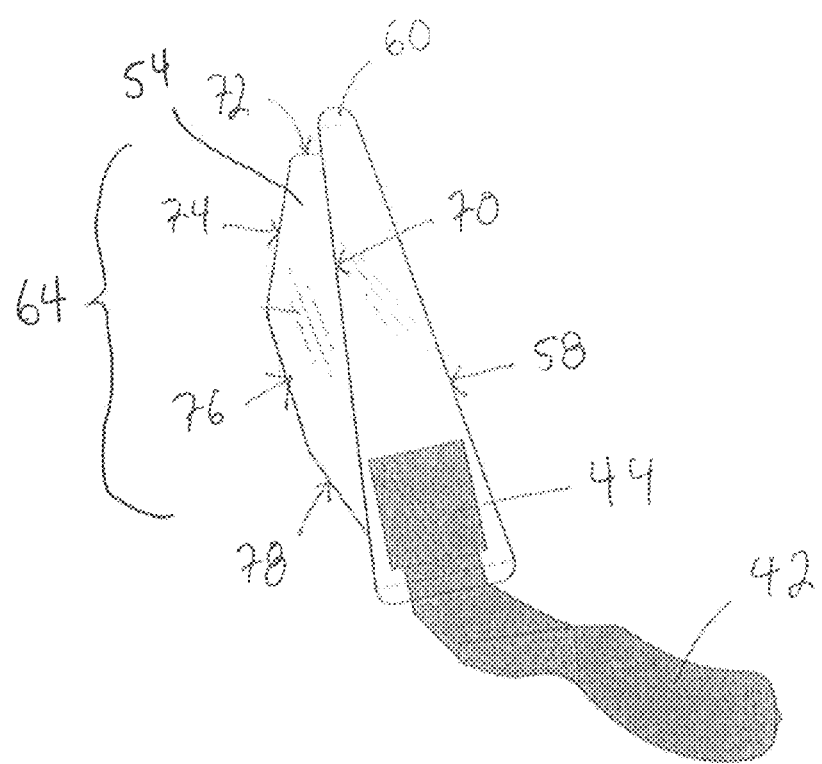
FIG. 3 is a side view of the wiper assembly of FIG. 2.

Shield assembly 50, shown in FIGS. 2 and 3, has a carriage 52 and a wiper 54. Carriage 52, as shown, is a conic structure from which wiper 54 extends. Carriage 52 need not be conical, as its function is to hold wiper 54 onto base 42 and therefore carriage 52 can have a variety of shapes. The conic shape illustrated is for aesthetic purposes.

Carriage 52 has a base 56, a curved surface 58, and vertex 60. A bore 62 into base 56 is configured to receive boss 44. Accordingly, bore 62 is preferably circular in cross section, having approximately the same radius as boss 44 if boss 44 is cylindrical, but can be other shapes to accommodate boss 44. Vertex 60 is preferably rounded instead of pointed, to prevent injury.

Wiper 54 extends normally from curved surface 58. Wiper 54 preferably is configured to complement the contour of cup 30. Cup 30, as is conventional in the art, has a central section with a diameter smaller than the diameter at the distal and proximal ends of the cup. Wiper 54, then, as shown in FIGS. 2 and 3, has a point forming an obtuse angle. As prophy cup 30 rotates, wiper 54 removes slurry from the outer edge of prophy cup 30.

As illustrated in FIGS. 2 and 3, wiper 54 has an irregular polygonal shape defined by a plurality of line segments. Line segment 70 has a length shorter than the slant height of curved surface 58. Line segment 72 extends a short distance from line segment 70, preferably at 90 degrees. Line segment 74 and line segment 76 form an obtuse angle, the vertex of which is farther from curved surface 58, measured normally, than any other point of wiper 54. Line segment 78 then reconnects to line segment 70. Wiper 54 is therefore an irregular pentagon as illustrated, but other shapes can be used to complement the shape of cup 30.

Line segments 74, 76, and 78 define a perimeter 64 of wiper 54 that has clearance from zero (or no clearance) to about 0.4 mm from prophy cup 30. Perimeter 64 preferably has a rounded edge. Perimeter 64, being complementary to the shape of cup 30, removes fluid from the outer surface of prophy cup 30 as prophy cup 30 rotates.

The method of manufacture of wiper assembly 20 is the following steps, not necessarily in this order:

Step 102. Base 42 is injection molded, preferably from a material similar to the material of neck section 24.

Step 104. Shield assembly 50 is preferably over-molded onto base 42 to produce wiper assembly 40. Alternatively, shield assembly 50 can be separately injection molded and then glued onto base 42 to produce wiper assembly 40. The wiper is made using a flexible material, while the base is made from a rigid material that is compatible with the prophy angle body.

Step 106. Base 42 of wiper assembly 40 is then glued or ultrasonic-welded to neck section 24.

Preferably, base 42 is made of a rigid material, such as a polycarbonate or a polyethylene or similar material. Most preferably, base 42 is made from a material having a hardness of about 60 to 90 Shore D (see ASTM D2240).

Preferably, shield assembly 50 is made of a less rigid material than that of base 42, such as a thermoplastic elastomer, a liquid silicone rubber, or similar material. Most preferably, shield assembly 50 is made from a material having hardness of about 35 to 65 Shore A (see ASTM D2240.)

The use of a separate base and wiper components produces surprising results. Most prophy angles are made of relatively hard plastic such as polycarbonate. A wiper is conventionally made of a more flexible material such as a thermoplastic elastomer, as it must conform to the shape of a prophy cup and not cause damage to the prophy cup. But to attach a piece made of one material to a second piece made of another material, using glue or ultrasonic welding, the two materials must be relatively similar. Accordingly, the wiper used by Kumar in the '102 Patent must be attached by a recessed channel, as that wiper cannot easily be glued or ultrasonically welded to Kumar's neck section. The use in the present invention of base 42 made of a material such as polycarbonate allows base 42 to attach securely to neck section 24.

The method of assembly of the present invention also produces the surprising result of much more efficient manufacture. An individual dental handpiece manufacturer will generally have a plurality of models of different prophy angle tools. If the manufacturer has six models, for example, it needs six sets of molds. To convert each tool to have a wiper option requires new tooling for every different model, as described above, requiring the manufacturer to obtain and maintain 12 sets of mold. Use of the method of present invention allows the manufacturer to make the wiper independently of the dental prophy appliance, and then optionally to attach the wiper via gluing or ultrasonic welding, so no new molds are required for the body of the handpiece. The manufacturer then can sell prophy angles without wipers and prophy angles with wipers, with the investment of only minimal additional capital expenditures. The additional equipment needed is a two-shot mold for base and wiper, and a small assembly machine to weld or glue the assembled part to existing dental prophy appliances. Accordingly, the design of the present invention can be used to retrofit any dental prophy appliance style to a new wiper style with much lower capital investment.

While preferred embodiments of the present invention are shown and described, it is envisioned that those skilled in the art may devise various modifications of the present invention without departing from the spirit and scope of the appended claims.

I claim:

1. A method of manufacturing a dental prophy angle having a wiper assembly, the method comprising the steps of:
   manufacturing the dental prophy angle, the dental prophy angle comprising a neck section, the neck section having an outer surface;
   manufacturing a wiper assembly by:
      molding a base, the base having an undersurface, the undersurface configured to match the outer surface of the neck section;
      over-molding a shield assembly onto the base, the shield assembly comprising a carriage and a wiper;
   attaching the undersurface to the outer surface.

2. The method of claim 1, wherein the attaching step comprises at least one of gluing and ultrasonic welding.

3. The method of claim 1, wherein the neck section comprises a first material and the base comprises a second material, the first material and the second material having a similar hardness.

4. The method of claim 3, wherein the first material and the second material have a hardness of 60 to 90 Shore D.

5. The method of claim 3, wherein the shield assembly comprises a third material, the third material being more flexible than the first material and the second material.

6. The method of claim 5, wherein the third material has a hardness of 35 to 65 Shore A.

7. The method of claim 4, wherein the shield assembly comprises a third material, the third material having a hardness of 35 to 65 Shore A.

8. A method of manufacturing a dental prophy angle having a wiper assembly, the method comprising the steps of:
   manufacturing the dental prophy angle, the dental handpiece comprising a neck section, the neck section having an outer surface;
   manufacturing a wiper assembly by:
     molding a base, the base having an undersurface, the undersurface configured to match the outer surface of the neck section;
     molding a shield assembly, the shield assembly comprising a carriage and a wiper;
     attaching the base to the shield assembly; and
     attaching the undersurface to the outer surface.

9. The method of claim 8, wherein the attaching-the-undersurface step comprises at least one of gluing and ultrasonic welding.

10. The method of claim 8, wherein the neck section comprises a first material and the base comprises a second material, the first material and the second material having a similar hardness.

11. The method of claim 10, wherein the first material and the second material have a hardness of 60 to 90 Shore D.

12. The method of claim 10, wherein the wiper comprises a third material, the third material being more flexible than the first material and the second material.

13. The method of claim 12, wherein the third material has a hardness of 35 to 65 Shore A.

14. The method of claim 11, wherein the wiper comprises a third material, the third material having a hardness of 35 to 65 Shore A.

* * * * *